United States Patent [19]

Beineke

[11] Plant 4,966

[45] Dec. 21, 1982

[54] BLACK WALNUT TREE

[75] Inventor: Walter F. Beineke, West Lafayette, Ind.

[73] Assignee: Purdue Research Foundation, West Lafayette, Ind.

[21] Appl. No.: 254,906

[22] Filed: Apr. 16, 1981

[51] Int. Cl.[3] ..... A01H 5/03

[52] U.S. Cl. ..... Plt./32

[58] Field of Search ..... Plt./32

*Primary Examiner*—Robert E. Bagwill

*Attorney, Agent, or Firm*—John R. Nesbitt

[57] ABSTRACT

A new and distinct cultivar of black walnut tree (*Juglans nigra L.*) which is distinctly characterized by extremely rapid growth rate, fair central stem tendency, earlier than average time of leafing, and average straightness thereby producing good timber qualities. The new variety has outstanding nut qualities as well, such as abundant annual crops of large-sized nuts, begins nut-bearing early in life of tree, average 2 nuts per cluster, and produces kernels which exceed about seventeen (17) percent of nut weight. The nuts are large and ripen early. The pistillate flowers mature early while pollen maturity is mid-season. In most years there is no overlap in female and male flowering. Flowering begins very early in the life of the tree. This new variety of black walnut tree was discovered by the applicant near Fritchton in Knox County, Ind., in a cultivated area. It occurred as a wild tree growing on land managed for timber-growing purposes and was discovered in the course of a search for unique and high quality black walnut trees to be utilized in breeding for outstanding timber producing potential. This selection has been designated as BW48 in records maintained on the performance of grafts made from the original selection and will be known henceforth as Knox-1.

3 Drawing Figures

BACKGROUND OF THE INVENTION

Figure 1:
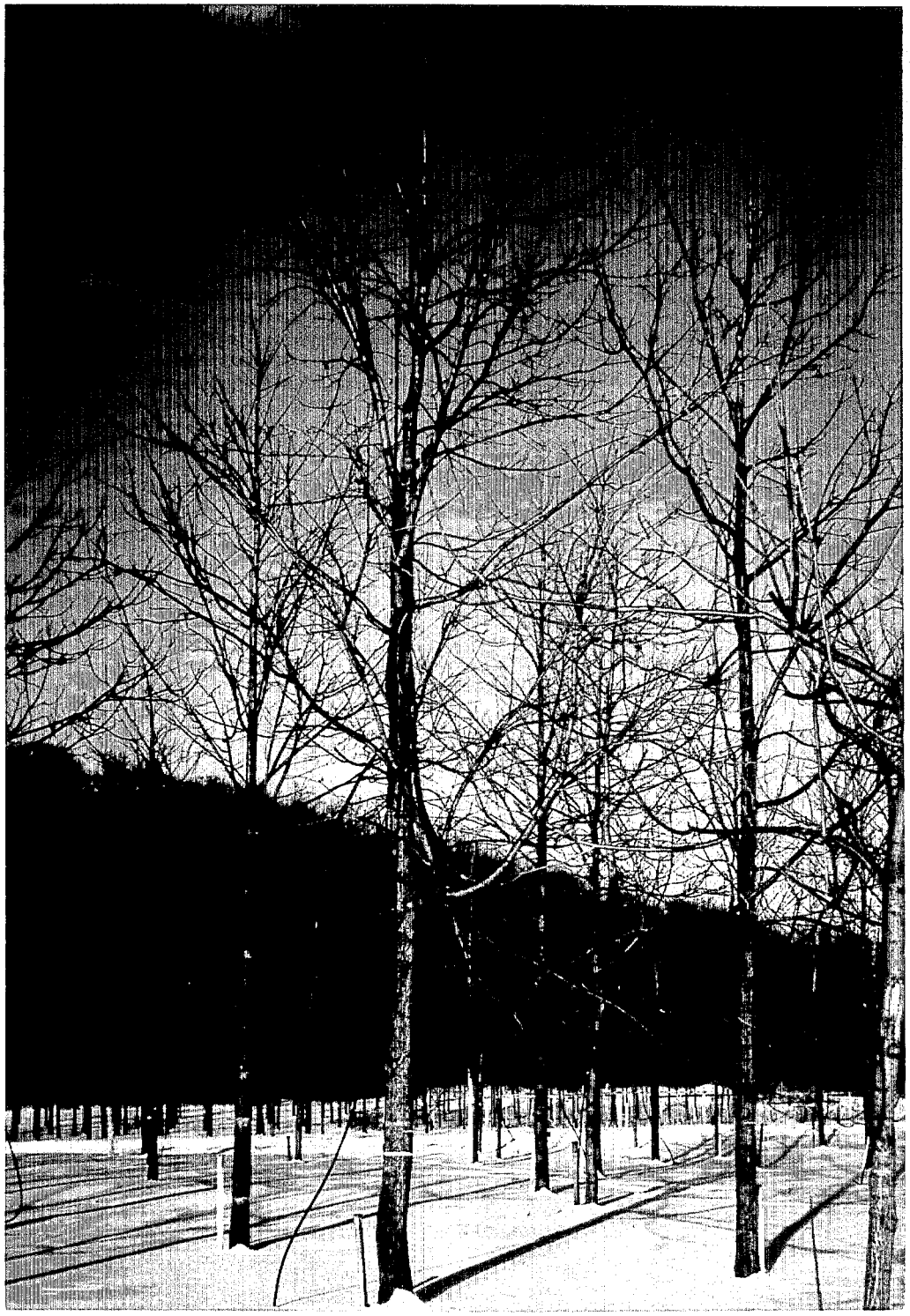
FIG. 1 is a photograph showing the timber form of Knox-1.
Figure 2:
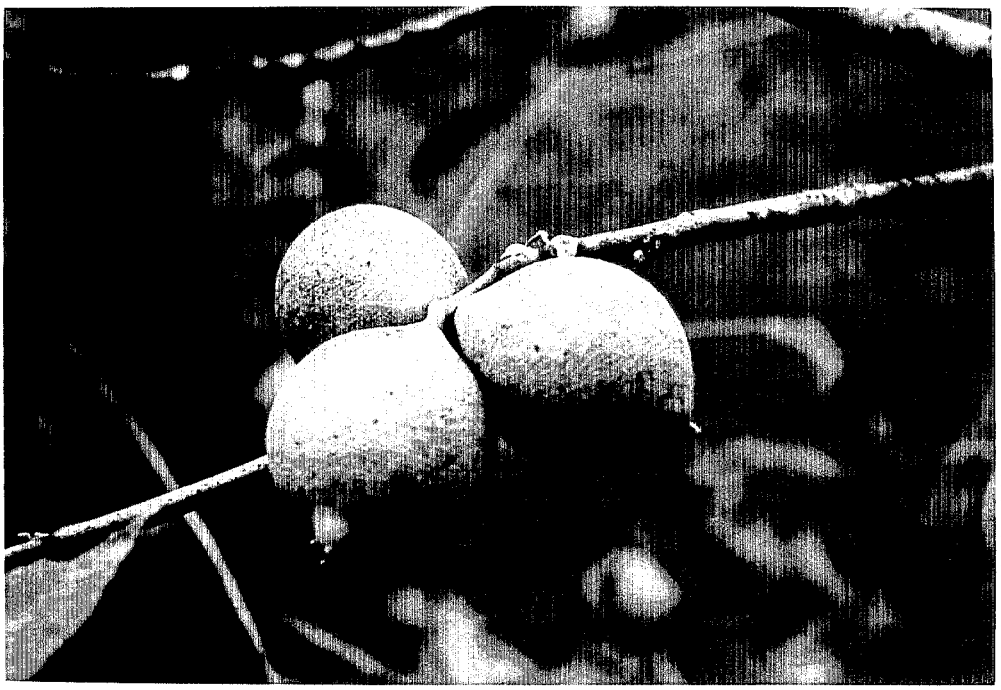
FIG. 2 is a photograph showing a twig with nuts attached from Knox-1.
Figure 3:
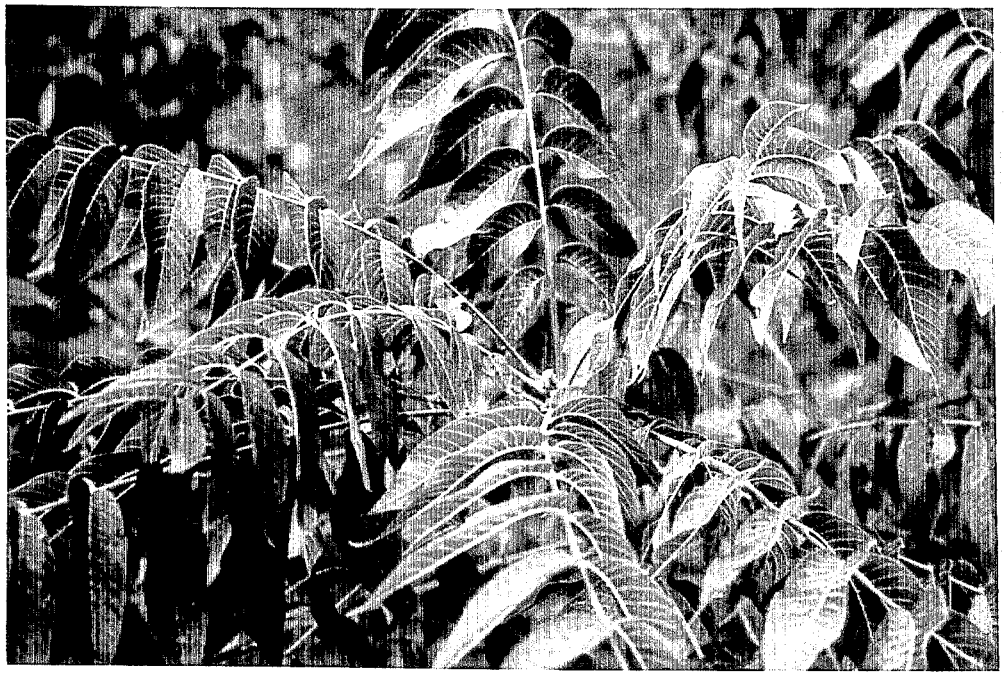
FIG. 3 is a photograph showing leaves from Knox-1.

After the original clone was selected, and assigned an identity number of BW48, the aforesaid tree was reproduced by collecting scions from it and grafting these onto common black walnut rootstocks at Martell Forest, Purdue University. These asexual reproductions ran true to the parent tree and to each other in all respects.

The botanical details of this new and distinct variety of walnut tree are as follows:

Tree:

*Size.*—Large.

*Vigor.*—Vigorous.

*Growth rate.*—Very rapid, somewhat faster than Purdue 1 — 23% larger in diameter than the average of selected clones planted the same year, 15% taller than the average, and 60% more cubic foot volume than the average.

*Form.*—Fair to poor timber form — only slightly better than average. May be slightly better than Purdue 2, but much poorer than Purdue 1 and 3. Averages 6% straighter than average on a rating scale of 1 to 5. Many crooks.

Trunk:

*Bark.*—Dark brown to gray.

*Texture.*—Interlacing ridges.

Branches:

*Diameter.*—Large.

*Length.*—Long.

*Branch angle.*—Lower branches — steep — 66 deg.

*Foliage.*—Quantity — abundant. Density — heavy.

Leaves:

*Compound leaves.*—Size — average; average length $17\frac{1}{2}''$.

*Leaflets.*—Size — large; average length — $4\frac{3}{8}''$; average width — $1\frac{3}{8}''$; average number of leaflets — 19; shape — lanceolate; acutely pointed. Thickness — thin; Texture — smooth; Margin — serrated; Petiole — short; Color — Topside 13 dark green; Underside — light green.

*Anthracnose resistance.*—Better than average on a rating scale of 1 to 5.

*Time of leafing.*—Very early — averages 5 to 6 days earlier or 54% earlier than average.

Flowering habit:

*Age at which tree starts producing catkins.*—Very early.

*Number of catkins produced.*—Abundant.

*Size of catkins.*—Large.

*Time of pollen shed.*—Average.

*Age at which time tree starts producing pistillate flowers.*—Very early.

*Number of pistillate flowers produced by young tree.*—Abundant.

*Number of pistillate flowers produced by mature tree.*—Abundant.

*Lateral shoots producing pistillate flowers.*—Few.

*Number of pistillate flowers per inflorescence.*—Averages 2 to 3.

*Timing of pistillate flower receptivity.*—Very early.

*Coincidence of staminate and pistillate bloom.*—Seldom.

Nut crop:

*Bearing.*—Annual.

*Productivity.*—Heavy.

*Ripening period.*—Early.

*Evenness of maturity (period between first and last nuts are ready for harvest).*—Even.

*Quality.*—Very good.

*Distribution of nuts on tree.*—Throughout.

Hull:

*Outer surface.*—Smooth — waxy.

*Form.*—Slightly pointed both ends — pear shape.

*Thickness.*—Medium.

*Size.*—Medium to large; average length — 2 7/16"; average diameter in suture plane — 1 15/16"; average diameter cheek to cheek — 2 3/32".

Nut:

*Size.*—Large; average length — 1½"; average diameter in suture plane — 1 7/32"; average diameter cheek to cheek — 1 7/16".

*Uniformity of size.*—Very uniform.

*Form.*—Oblong.

*Blossom end.*—Rounded.

*Basal end.*—Pointed.

*Weight.*—Dry weight of ten nuts — 173.8 gm; dry weight of ten kernels — 29.6 gm; average percentage of kernels to nuts — 17%.

*Thickness of shell.*—Medium.

*Fill.*—Good.

Kernel:

*Size.*—Large.

*Plumpness.*—Plump.

*Shrivel.*—None.

*Flavor.*—Good.

*Color.*—Light.

The walnut tree and its nuts herein described may vary in slight detail due to climatic and soil conditions under which the variety may be grown; the present description being of the variety as grown near West Lafayette, Ind.

I claim:

1. A new and distinct variety of black walnut tree substantially as illustrated and described, which has good timber quality, is very fast growing, has fair central stem tendency, earlier than average in time of leafing, pistillate flowers early, pollen sheds mid-season, produces abundant annual crops of large-size nuts; averages 2 per cluster, the percentage of weight of kernel to nut averages approximately 17 percent; nut bearing begins early in life of tree.

* * * * *